(12) United States Patent
Keusenkothen et al.

(10) Patent No.: US 9,260,361 B2
(45) Date of Patent: Feb. 16, 2016

(54) HYDROCARBON CONVERSION PROCESS

(71) Applicants: Paul F. Keusenkothen, Houston, TX (US); Frank Hershkowitz, Basking Ridge, NJ (US); S. M. Davis, Humble, TX (US)

(72) Inventors: Paul F. Keusenkothen, Houston, TX (US); Frank Hershkowitz, Basking Ridge, NJ (US); S. M. Davis, Humble, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 13/650,642

(22) Filed: Oct. 12, 2012

(65) Prior Publication Data

US 2013/0131409 A1 May 23, 2013

Related U.S. Application Data (60) Provisional application No. 61/562,600, filed on Nov. 22, 2011.

(51) Int. Cl.
| | |
|---|---|
| *C07C 2/76* | (2006.01) |
| *C07C 5/09* | (2006.01) |
| *C07C 4/02* | (2006.01) |
| *C07C 11/00* | (2006.01) |
| *C07C 5/333* | (2006.01) |
| *C07C 7/167* | (2006.01) |
| *C10G 50/00* | (2006.01) |
| *C10G 9/14* | (2006.01) |

(52) U.S. Cl.
CPC .............. *C07C 5/333* (2013.01); *C07C 7/167* (2013.01); *C10G 9/14* (2013.01); *C10G 50/00* (2013.01); *C10G 2300/1025* (2013.01); *C10G 2400/20* (2013.01)

(58) Field of Classification Search
USPC .......................................... 585/251
See application file for complete search history.

(56) References Cited

U.S. PATENT DOCUMENTS

| 3,267,170 | A | 8/1966 | Aldridge et al. | |
|---|---|---|---|---|
| 3,321,545 | A | 5/1967 | Rigney et al. | |
| 5,585,530 | A * | 12/1996 | Gough et al. | 585/257 |
| 5,639,926 | A | 6/1997 | Turner et al. | |
| 6,564,580 | B2 * | 5/2003 | Bowen et al. | 62/623 |
| 7,943,808 | B2 | 5/2011 | Hershkowitz et al. | |
| 2007/0191664 | A1 * | 8/2007 | Hershkowitz et al. | 585/539 |
| 2009/0198090 | A1 * | 8/2009 | Mamedov et al. | 585/324 |
| 2009/0247714 | A1 * | 10/2009 | Fritz et al. | 526/68 |
| 2010/0130803 | A1 * | 5/2010 | Keusenkothen et al. | 585/535 |
| 2011/0054231 | A1 * | 3/2011 | Peterson | 585/251 |

FOREIGN PATENT DOCUMENTS

| EP | 1 741 691 | 10/2007 |
|---|---|---|
| WO | WO 80/02558 | * 11/1980 |
| WO | WO8002558 | * 11/1980 |

OTHER PUBLICATIONS

Barker et al., Kirk-Othmer Encyclopedia of Chemical Technology, 2005, John Wiley and Sons, Inc.*
Kirk-Othmer Encyclopedia of Chemical Technology, "Ethylene," John Wiley & Sons, vol. 10, pp. 599-609.

(Continued)

*Primary Examiner* — In Suk Bullock
*Assistant Examiner* — Youngsul Jeong (57) ABSTRACT

The invention relates to processes for converting hydrocarbons to olefins products such as ethylene and propylene. The invention also relates to polymerizing the olefins, and to equipment useful for these processes.

17 Claims, 4 Drawing Sheets

(56) References Cited

OTHER PUBLICATIONS

Kamiński, A.M., React. Kinet. Catal. Lett., "Pyrolysis of Propane in the Presence of Acetylene", vol. 48, No. 1, pp. 309-313 (1992).

Iglesia, E. et al., Catalysis Letters, Hydrogen transfer and activiation of propane and methane on ZSM5-based catalysts, 21 (1993) pp. 55-70.

* cited by examiner

HYDROCARBON CONVERSION PROCESS

PRIORITY

The present application claims priority to U.S. Ser. No. 61/562,600, filed on Nov. 22, 2011, entitled, "Hydrocarbon Conversion Process" the entire disclosures of which are hereby incorporated by reference herein.

FIELD

The invention relates to processes for converting hydrocarbons to olefins products such as ethylene and propylene. The invention also relates to polymerizing the olefins, and to equipment useful for these processes.

BACKGROUND

Olefins, such as ethylene and propylene can be produced by conventional pyrolysis processes, such as steam cracking. Steam cracking involves exposing water and a hydrocarbon having at least two carbon atoms to a temperature in the range of about 600° C. to about 1100° C., a pressure in the range of about 1.5 to 2.75 bar, and a residence time in the range of 0.1 to 0.6 second. See, e.g., Kirk Othmer Encyclopedia of Chemical Technology, Vol. 10, 599-609. The reference discloses that steam cracking feeds comprising butane and light naphtha lead to an increase in the relative amount of propylene in the product. Although the reference discloses optimizing the process for increased propylene production, the relative amount of ethylene in the product is generally much larger than the amount of propylene.

European Patent Application Publication No. EP 1741691A1 discloses a two-step process for producing ethylene. According to that reference, high-temperature hydrocarbon pyrolysis is utilized to produce acetylene. Hydrogen is then thermally transferred from alkane to the acetylene, the hydrogen transfer being conducted at a temperature in the range of 800° C. to 910° C. When the alkane is propane, the hydrogen transfer produces ethylene and propylene.

Hydrocarbon pyrolysis and thermal hydrogen-transfer require a significant amount of energy. Hydrocarbon conversion processes utilizing less energy are desired. In certain cases, it is also desired to increase the relative amount of propylene in the product.

SUMMARY

In an embodiment, the invention relates to hydrocarbon conversion process, comprising:
(a) providing a first mixture comprising ≥10.0 wt. % hydrocarbon based on the weight of the first mixture;
(b) exposing the first mixture a temperature ≥1200° C. under pyrolysis conditions to produce a second mixture, the second mixture comprising ≥1.0 wt. % acetylene, based on the weight of the second mixture; and
(c) catalytically transferring hydrogen from a hydrogen donor to at least 10.0 wt. % of the second mixture's acetylene to produce ethylene, the weight percent being based on the weight of the second mixture's acetylene.

In another embodiment, the invention relates to a hydrocarbon conversion process, comprising:
(a) providing a natural gas comprising ≥10.0 wt. % methane and ≥5.0 wt. % ethane based on the weight of the natural gas;
(b) separating ethane from the natural gas to produce a first mixture comprising ≥10.0 wt. % methane based on the weight of the first mixture;
(c) exposing the first mixture a temperature ≥1200° C. under pyrolysis conditions to produce a second mixture, the second mixture comprising ≥1.0 wt. % acetylene, based on the weight of the second mixture; and
(d) producing ethylene by catalytically transferring hydrogen from at least a portion of the separated ethane to at least 10.0 wt. % of the second mixture's acetylene based on the weight of the second mixture's acetylene. Optionally, the method further comprises polymerizing at least a portion of the ethylene produced in step (d).

DETAILED DESCRIPTION

One embodiment of the invention relates to a process for producing a second mixture comprising acetylene and ethylene by pyrolysing a first mixture comprising hydrocarbon (e.g., methane) at a temperature ≥1200° C. (wherein ≥1200° C. means ≥1.20×10³° C., i.e., three significant digits) and then catalytically transferring hydrogen from a hydrogen donor to at least a portion of the second mixture's acetylene. The hydrogen donor can be, e.g., a $C_{2+}$ alkane such as ethane or propane. For example, hydrogen can be transferred catalytically from propane to at least a portion of the second mixture's acetylene to produce a product comprising propylene and ethylene, the product having (on a molar basis) a greater propylene content and a lesser acetylene content than the second mixture. In an embodiment, the second mixture comprises ≥1.0 wt. % acetylene based on the weight of the second mixture, and the hydrogen-transfer catalyst comprises a catalytically-effective amount of at least one catalytic metal and an inorganic support.

Optionally, the process has one or more of the following features, (i) the second mixture has an acetylene:ethylene molar ratio ≥1.6, e.g., ≥1.75, such as ≥2.0; (ii) ≥50.0 wt. %, e.g., ≥75.0 wt. %, such as ≥90.0 wt. % of the second mixture's acetylene is converted to monoolefin by catalytically transferring hydrogen from the hydrogen donor to the acetylene based on the weight of acetylene in the second mixture; or (iii)

the first mixture's hydrocarbon and the hydrogen donor are both derived from substantially the same source material, e.g., natural gas.

It has been found that the process utilizes less energy to produce, more monoolefin with fewer combustible non-volatiles than the conventional process of high-temperature pyrolysis followed by thermal hydrogen transfer from alkane to acetylene. While not wishing to be bound by any theory or model, it is believed that these features result from the relatively mild catalytic hydrogen transfer conditions, e.g., a temperature in the range of 200° C. to 600° C. and a pressure in the range of 1.0 bar to 10.0 bar when utilizing a heterogeneous hydrogen transfer catalyst. The catalytic hydrogen transfer catalyst and process conditions can be the same as those disclosed in U.S. Pat. No. 5,585,530, which is incorporated by reference herein in its entirety. Optionally, the catalytic hydrogen transfer (i) is thermally neutral or exothermic and (ii) has ≥50% selectivity (on a molar basis) for converting the acetylene to ethylene.

Figure 1:
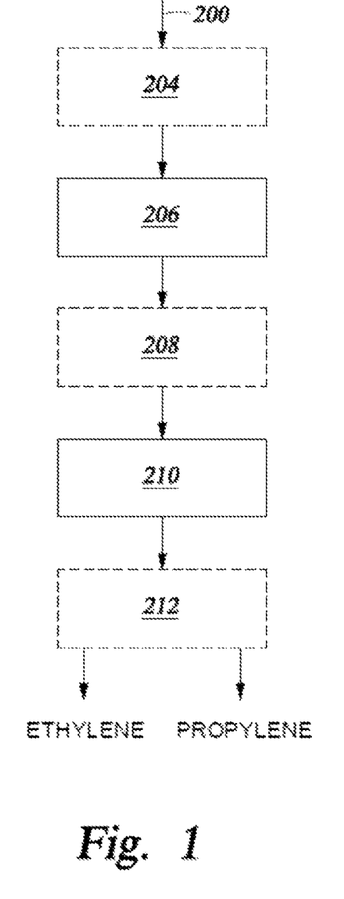
FIG. 1 schematically illustrates embodiments of the invention relating to the production of ethylene and acetylene by pyrolysis of a first mixture comprising hydrocarbon. The ethylene is polymerized to produce, e.g., polyethylene. Hydrogen is catalytically transferred from propane to the acetylene to produce propylene, which is then polymerized to produce, e.g., polypropylene. Optional stages are enclosed by dashed boundaries.

FIG. 1 schematically illustrates one representative embodiment wherein at least a portion of a first mixture obtained from a hydrocarbon source 200 is converted to ethylene and propylene. The first mixture is conducted to pyrolysis stage 206 for converting at least a portion of the first mixture's hydrocarbon to a pyrolysis product (the second mixture) comprising acetylene. Optionally, the source material is upgraded, e.g., in optional upgrading stage 204, which can be utilized for removing one or more undesired species from the source material (such as hydrogen sulfide and/or carbon dioxide) to produce the first mixture. At least a portion of any non-acetylene species present in the second mixture, such as methane, can be removed in optional treatment stage 208. A hydrogen donor comprising propane and at least a portion of the second mixture's acetylene are conducted to catalytic hydrogen-transfer stage 210, where hydrogen is transferred from at least a portion of the propane to at least a portion of the acetylene to produce a hydrogen-transfer product comprising propylene and ethylene. Optionally, the hydrogen-transfer product has an acetylene:ethylene molar ratio that is less than that of the second mixture, e.g., ≤0.5 times the second mixture's acetylene:ethylene molar ratio. The propylene and/or ethylene can be separated from the hydrogen-transfer product in optional separation stage 212. The ethylene and/or propylene can be polymerized or copolymerized if desired, e.g., to make polymer comprising one or more of polyethylene, polypropylene, or ethylene-propylene copolymer.

Figure 2:
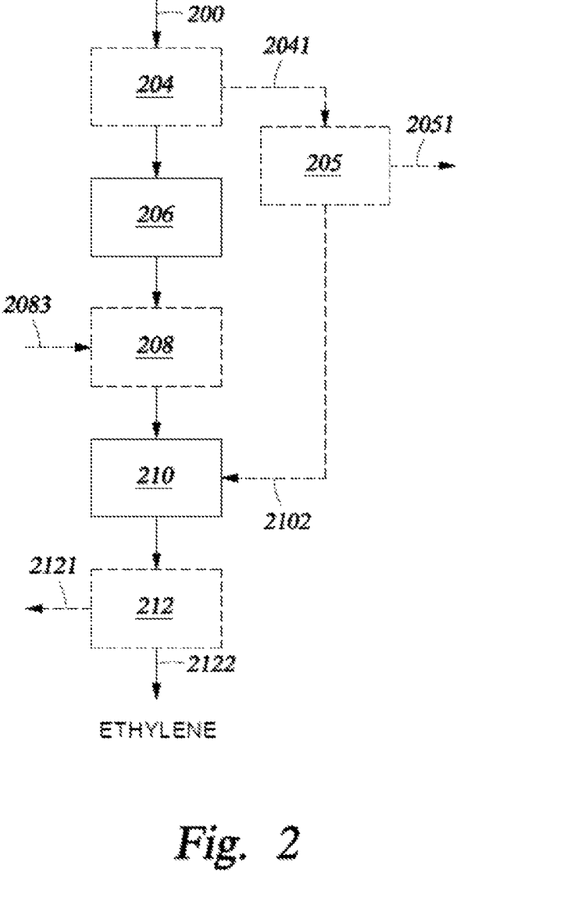
FIG. 2 schematically illustrates an embodiment utilizing a source material comprising methane and ethane. In this embodiment, the first mixture comprises methane and the hydrogen donor comprises ethane, at least a portion of the first mixture's methane and the hydrogen donor's ethane being obtained from the source material. Hydrogen is catalytically transferred from the ethane to the acetylene to produce ethylene, which is then polymerized to produce, e.g., polyethylene. Optional stages are enclosed by dashed boundaries.

In another embodiment of the invention, illustrated in FIG. 2, the first mixture and the hydrogen donor are derived from a source material 200, the source material comprising methane and one or more saturated $C_{2+}$ hydrocarbon such as ethane. For example, the source material 200 can be a natural gas comprising ≥10.0 wt. % methane and ≥1.0 wt. % ethane based on the weight of the source material. At least a portion of the source material's ethane is separated in stage 204 and conducted away via conduit 2041, to produce a first mixture comprising at least a portion of the source material's methane. The first mixture is exposed to a temperature ≥1200° C. in pyrolysis stage 206 to produce a pyrolysis product (the second mixture) comprising acetylene. At least a portion of the second mixture's acetylene is conducted to hydrogen transfer stage 210. At least one hydrogen donor is conducted to catalytic hydrogen-transfer stage 210 via conduit 2102. As shown, the hydrogen donor utilized in stage 210 comprises at least a portion of the ethane separated from the hydrocarbon source material in stage 204. When more ethane is separated in stage 204 than is desired in stage 210, excess ethane can be separated and conducted away upstream of stage 210, e.g., via optional splitter 205 and conduit 2051. Hydrogen transfer from the ethane to the acetylene results in the conversion to a hydrogen-transfer product comprising ethylene of (i) at least a portion of the hydrogen donor's ethane and (ii) at least a portion of the second mixture's acetylene. Ethylene can be separated from the hydrogen-transfer product in optional stage 212. The process encompasses polymerizing at least a portion of the ethylene.

In a related embodiment, a utility fluid, e.g., a utility fluid comprising a polar solvent, is conducted to stage 208 via conduit 2083, where the utility fluid is utilized for extracting at least a portion of the second mixture's acetylene. A raffinate comprising (i) at least a portion of the non-acetylene components of the pyrolysis product and optionally (ii) a portion of the pyrolysis product's acetylene is conducted away from stage 208. An extract comprising at least a portion of the utility fluid and at least a portion of the second mixture's acetylene is conducted to catalytic hydrogen-transfer stage 210 for hydrogen transfer from the ethane to the acetylene, the catalytic hydrogen transfer optionally being conducted in the liquid-phase. Ethylene can be separated from the hydrogen-transfer product in stage 212, with the utility fluid conducted away via conduit 2121, e.g., for regeneration and/or re-use in stage 208. Separation of the ethylene from the hydrogen-transfer product can be aided by selecting a utility fluid having solubility for ethylene (at separation temperature and pressure) that is ≤0.5 times the utility fluid's acetylene solubility at substantially the same temperature and pressure. Should the raffinate comprise ethylene, that ethylene can be separated from the raffinate and polymerized, either alone or, e.g., in combination with ethylene obtained from the hydrogen-transfer product. When the hydrogen donor comprises an alkane mixture, e.g., a mixture of ethane and propane, the hydrogen-transfer product can comprise a mixture of ethylene and propylene, e.g., a mixture comprising ≥1.0 wt. % ethylene, such as 5.0 wt. % ethylene; ≥1.0 wt. % propylene, such as 5.0 wt. % propylene; and unreacted acetylene and/or unreacted propane.

In any of the preceding embodiments, at least a portion of the first mixture's hydrocarbon and at least a portion of the hydrogen donor can be obtained from the same source material(s). For example, (i) the first mixture can comprise, e.g., ≥10.0 wt. %, e.g., 50.0 wt. %, such as 75.0 wt. % methane obtained from a source material, based on the weight of the first mixture, and (ii) the hydrogen donor can comprise, e.g., ≥10.0 wt. %, e.g., 50.0 wt. %, such as 75.0 wt. % ethane obtained from the source material, based on the weight of the hydrogen donor. The first mixture can be exposed to a temperature ≥$1.40 \times 10^{3}$° C. under pyrolysis conditions to produce a second mixture comprising ≥0.5 wt. % ethylene and ≥0.5 wt. % acetylene based on the weight of the second mixture, the second mixture having an acetylene:ethylene molar ratio $A_1$. Hydrogen is catalytically transferred from at least a portion of the hydrogen donor's ethane to at least a portion of the second mixture's acetylene to produce a product having an acetylene:ethylene molar ratio $A_2$, wherein $A_2 \leq 0.5 * A_1$. Since pyrolysis is endothermic, the process utilizes significantly less energy to produce the same amount of ethylene (on a weight basis) than would be the case if the source material's ethane and methane were together subjected to the pyrolysis. When the hydrogen donor comprises ≥10.0 wt. %, e.g., 50.0 wt. %, such as 75.0 wt. % propane, based on the weight of the hydrogen donor, the catalytic hydrogen transfer is optionally conducted under exothermic conditions having an enthalpy change in the range of 1.0 to 5.0 kcal/mole of converted propane. Optionally, at least a portion of the heat released by the catalytic hydrogen transfer is utilized in the endothermic pyrolysis reaction which produces the acetylene.

In an embodiment, the feed to the hydrogen-transfer step comprises first and second components, the first component comprising acetylene and the second component comprising at least one hydrogen donor. The first component can comprise, e.g., the second mixture and/or a third mixture, the third mixture comprising acetylene derived from the second mixture, such as by removing (e.g., by separation) at least a portion of the second mixture's acetylene. Optionally, the third mixture further comprises (i) one or more compositions removed from the second mixture, e.g., those such as diluent that may be useful for the hydrogen-transfer step and/or (ii) one or more compositions obtained from source(s) other than the second mixture. At least a portion of the first component can be combined with at least a portion of the second component upstream of the hydrogen-transfer step, but this is not required, and in one embodiment there is no significant mixing of the first and second components upstream of the hydrogen transfer.

For the purpose of this description and appended claims, the following terms are defined. The term "hydrocarbon" means molecules (and mixtures thereof) including both carbon atoms and hydrogen atoms, and optionally including other atoms (heteroatoms), such as oxygen, sulfur, and nitrogen. The term "molecular hydrogen" means $H_2$. The term "molecular oxygen" means $O_2$. The term "hydrogen donor" does not include molecular hydrogen.

The "Periodic Table of the Elements" means the Periodic Chart of the Elements as tabulated on the inside cover of The Merck Index, 12th Edition, Merck & Co., Inc., 1996.

The term "pyrolysis" means an endothermic reaction conducted at a temperature sufficient for thermally breaking C—C or C—H bonds, optionally aided by a catalyst, e.g., the conversion of hydrocarbons to unsaturates, such as ethylene and acetylene. The terms reactor, reactor system, regenerator, recuperator, regenerative bed, monolith, honeycomb, reactant, fuel, and oxidant have the meanings disclosed in U.S. Pat. No. 7,943,808, which is incorporated by reference herein in its entirety. The term "pyrolysis reactor", as used herein, refers to a reactor, or combination or system thereof for converting hydrocarbons by at least pyrolysis. The term pyrolysis reactor encompasses, e.g., the combination and system of first and second pyrolysis reactors described in U.S. Pat. No. 7,943,808. With respect to pyrolysis reactors, the term "residence time" means the average time duration for non-reacting (non-converting by pyrolysis) molecules (such as He, $N_2$, Ar) having a molecular weight in the range of 4 to 40 to traverse a pyrolysis region of a pyrolysis reactor. The pyrolysis region can include, e.g., one or more conduits, channels, or passages. The term "conduit" refers to means for conducting a composition from one location to another. The term encompasses (i) elementary conducting means, such as a pipe or tube, and (ii) complex means such as tortuous pathways through conducting means, e.g., pipes, tubes, valves, and reactors, that are filled with random packing. The term "passage" means a geometrically contiguous volume element that can be utilized for conveying a fluid within a reactor, regenerator, recuperator, regenerative bed, monolith, honeycomb, etc. The term "channel" means a plurality of passages that can be utilized together for conveying a fluid within the reactor, regenerator, recuperator, regenerative bed, monolith, honeycomb, etc. For example, a honeycomb monolith can comprise a single channel, the channel having a plurality of passages or sets of passages, e.g., hundreds of thousands of passages per square meter of the honeycomb's cross-section.

The term "pyrolysis stage" means at least one pyrolysis reactor, and optionally means for conducting one or more feeds thereto and/or one or more products away therefrom. The term "thermal pyrolysis" means <50.0% of the heat utilized by the pyrolysis is provided by (a) exothermically reacting the pyrolysis feed, e.g., by exothermically reacting an oxidant with hydrocarbon and/or hydrogen in the pyrolysis feed and/or (b) contacting the pyrolysis feed with the gaseous and/or liquid products of combustion to heat the pyrolysis feed. For example, in thermal pyrolysis ≥50.0% of the heat utilized by the pyrolysis is provided by heat transfer from reactor components, e.g., solid surfaces associated with a pyrolysis reactor; optionally ≥80.0% or ≥90.0% of the heat utilized by the pyrolysis is provided by such heat transfer. Optionally, exothermic oxidation, e.g., combustion, occurs within the thermal pyrolysis reactor.

The term "high-severity" with respect to pyrolysing a pyrolysis feed such as the first mixture means pyrolysis conditions resulting in the conversion of the mixture to make a product having an acetylene content ≥10.0 wt. % based on the weight of the hydrocarbons in the pyrolysis feed. The term "peak pyrolysis gas temperature" means the maximum temperature achieved by the bulk pyrolysis stream gases as they travel through the pyrolysis reactor (e.g., a cracking region or radiant region). One skilled in the art will appreciate that temperatures immediately proximate to a partition may be higher, and may, in some infinitesimal layer, actually approach the partition's temperature. However, the pyrolysis temperature referred to herein should be considered a bulk gas temperature, which is a temperature that could be measured by a device (such as a thermocouple) that is not in contact with the partition. For example, if the gas is traveling through tubulars in a thermal pyrolysis reactor, the bulk gas temperature may be taken as the average temperature over any tubular cross-section, and the peak pyrolysis gas temperature as the highest cross-sectional average temperature of the pyrolysis stream.

The second mixture is generally derived by thermal pyrolysis of the first mixture, the first mixture being derived from one or more source materials. The term "source materials" means one or more sources comprising hydrocarbon, including, e.g., one or more of petroleum-derived streams; syngas (a mixture comprising carbon monoxide and hydrogen), methane; methane-containing streams such as coal bed methane, biogas, associated gas, natural gas, and mixtures or components thereof; synthetic crudes; shale oils; or hydrocarbon streams derived from plant or animal matter. Suitable hydrocarbon source materials include those described in U.S. Pat. Nos. 7,943,808 and 7,544,852, which are incorporated by reference herein in their entirety.

Optionally, one or more mixtures and/or source materials comprise hydrogen atoms. The term "hydrogen content" of a mixture or source material means atomic hydrogen bound to carbon and/or heteroatoms covalently bound thereto and which excludes molecular hydrogen ($H_2$) in the mixture (or source material) expressed as a weight percent based on the weight of the hydrocarbons in the mixture (or source material). Optionally, one or more mixtures and/or source materials comprises non-volatiles. The term "non-volatiles" means molecules and mixtures thereof having a nominal atmospheric boiling point ≥570.0° C., e.g., refractory oxygenates, refractory hydrocarbon, metals, minerals, etc. American Society of Testing and Materials ("ASTM") methods can be used to determine the nominal atmospheric boiling point (ASTM method 1078) and the amount and properties of such non-volatiles, such as ASTM methods D-6560, D-7061, D-189, D-482, D-524, and D-2415. Non-volatiles that are capable of being combusted are called "combustible non-volatiles". The term non-volatiles encompasses e.g., coke, ash, soot, resid, metal, mineral, ash-forming asphaltenic, tar, etc., including those formed, e.g., during or after oxidation (such as combustion or partial oxidation) and/or pyrolysis, including those which may remain as a residue or deposit in the reaction region. The term "$C_2$ unsaturates" means hydrocarbon having two carbon atoms and two or four hydrogen atoms.

In an embodiment, the invention relates to a process for converting a first mixture comprising hydrocarbon by exposing the first mixture a temperature $\geq 1.20 \times 10^{3}$° C. under pyrolysis conditions to produce a second mixture, wherein the second mixture comprises $\geq 1.0$ wt. % acetylene, based on the weight of the second mixture (the pyrolysis step). The process further comprises catalytically transferring hydrogen from a hydrogen donor to at least a portion of the second mixture's acetylene (the hydrogen-transfer step). Optionally, the process further comprises at least one oxidation step, e.g., to provide heat for the pyrolysis. A regenerative, reverse-flow pyrolysis process useful for producing a second mixture comprising acetylene will now be described in more detail. The invention is not limited to this type of pyrolysis, and this description is not meant to foreclose the use of other types of pyrolysis processes within the broader scope of the invention.

Producing Acetylene in a Regenerative, Reverse-Flow Thermal Pyrolysis Reactor System In one or more embodiments, a regenerative, reverse-flow, thermal pyrolysis reactor system (illustrated in FIG. 3) is utilized for pyrolysing a first mixture comprising hydrocarbon to produce a second mixture compressing acetylene. The pyrolysis step comprises (a) exposing a first mixture comprising $\geq 10.0$ wt. % of hydrocarbon based on the weight of the first mixture to a temperature $\geq 1.20 \times 10^{3}$° C., e.g., $\geq 1.40 \times 10^{3}$° C., under thermal pyrolysis conditions in a first region 2064 of at least one regenerative, reverse-flow pyrolysis reactor in pyrolysis stage 206 and (b) conducting away from the first region at least a portion of a second mixture, the second mixture being derived from the first mixture by the pyrolysis, wherein the second mixture comprises $\geq 1.0$ wt. % of acetylene based on the weight of the second mixture. The pyrolysis can be conducted, e.g., under high-severity thermal pyrolysis conditions. At least a portion of the heat utilized for the pyrolysis is obtained from an oxidation step, which comprises (i) mixing first and second reactants to produce a fourth mixture, the first reactant comprising fuel and the second reactant comprising oxidant and then (ii) exothermically reacting at least a portion of the fourth mixture's fuel component with at least a portion of the fourth mixture's oxidant component in a second region 2063 of the reverse-flow, regenerative pyrolysis reactor to produce heat and a fifth mixture comprising, e.g., products of the oxidation. The exothermic reacting of the fourth mixture's fuel and oxidant provides $\geq 50.0\%$ of the heat utilized in the first region for deriving the second mixture from the first mixture.

Figure 3:
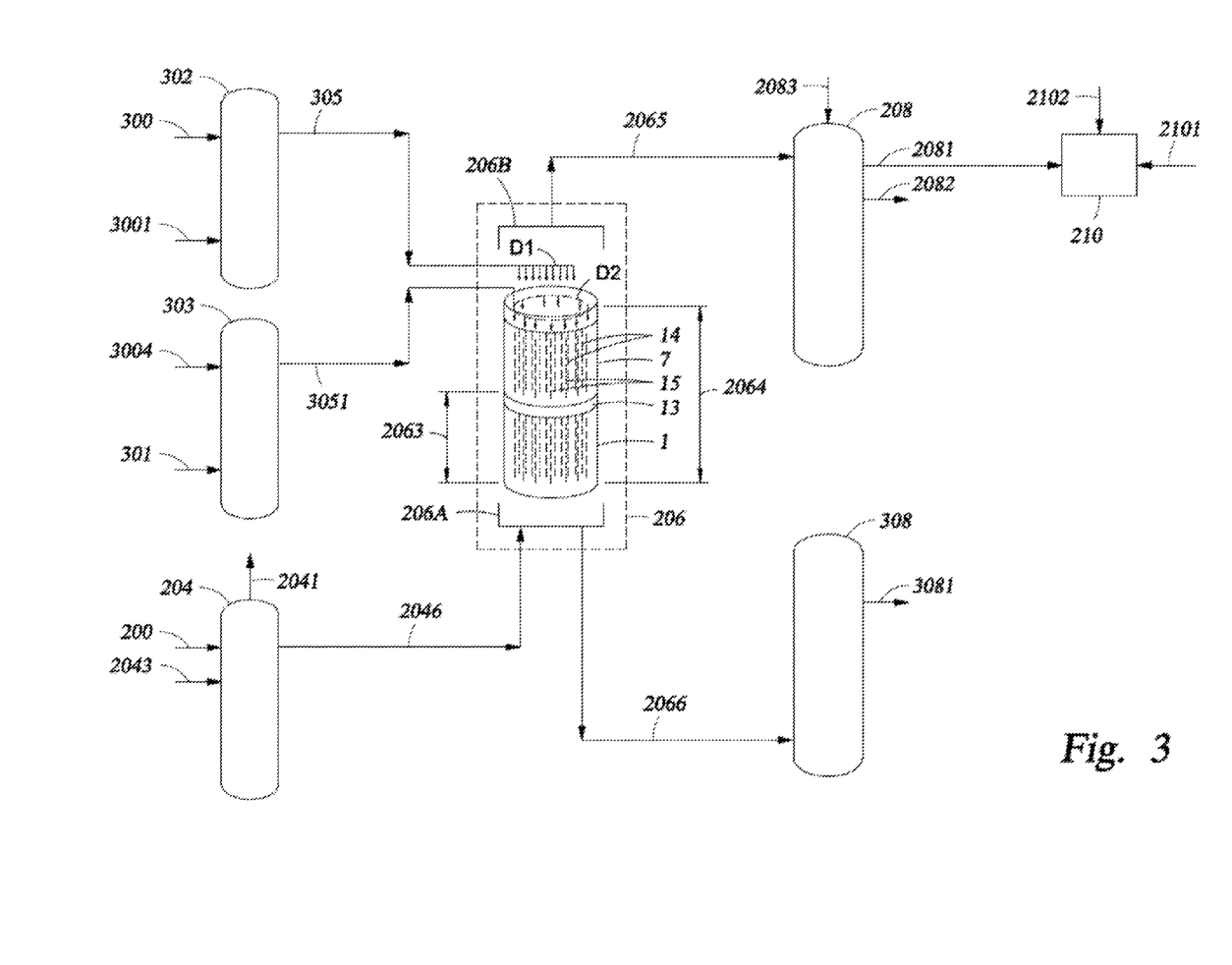
FIG. 3 schematically shows an embodiment of the invention utilizing a regenerative, reverse-flow pyrolysis system for producing acetylene.

The first and second regions can be at least partially coextensive, as shown in FIG. 3. The oxidation step and the pyrolysis step can be operated in sequence (e.g., one after the other). The sequence of oxidation step-pyrolysis step (or the reverse sequence) can be operated continuously. One or more optional steps, e.g., a step utilized from removing the fifth mixture from the pyrolysis reactor before introducing the first mixture (e.g., using a sweep gas) can be utilized before and/or after the oxidation step, the pyrolysis step, or both. The first mixture will now be described in more detail.

First Mixture

The first mixture generally comprises hydrocarbon and optionally further comprises molecular hydrogen and/or diluent. The first mixture can be derived from the source material(s) located upstream of the pyrolysis, but this is not required. For example, in one embodiment hydrocarbon derived from a first source material and molecular hydrogen derived from a second source material are conducted separately to the pyrolysis reactor, the hydrocarbon and molecular hydrogen being combined to produce the first mixture proximate to (e.g., within) the pyrolysis reactor. Optionally, the hydrocarbon has (or is derived from one or more source materials having), e.g., a hydrogen content (i) in the range of 6.0 wt. % to 25.0 wt. %, 8.0 wt. % to 20.0 wt. %, or (ii) in the range of 20.0 wt. % to 25.0 wt. %. Hydrogen content is determined in accordance with ASTM D4808-01 (2006). In a particular embodiment, the hydrocarbon of the first mixture is derived from (i) natural gas (e.g., a methane-containing gas of synthetic and/or geological origin) and/or (ii) aromatic gas oil ("AGO", wherein AGO means hydrocarbon wherein $\geq 1.0$ wt. %, e.g., 5.0 wt. %, such as 10.0 wt. % of the hydrocarbon's carbon atoms are included in an aromatic ring, based on the weight of the hydrocarbon).

The first mixture can comprise, e.g., upgraded natural gas (such as natural gas that has been sweetened and/or dehydrated). Besides methane, natural gas commonly includes other hydrocarbons (such as ethane and other alkanes), e.g., in amounts that can be less than, greater than, or substantially equal to the amount of methane in the natural gas on a weight basis.

Optionally, the first mixture further comprises diluent, e.g., $\geq 1.0$ wt. % of diluent based on the weight of the first mixture. Suitable diluents (which can be a diluent mixture) include one or more of molecular hydrogen, hydrogen sulfide, oxygenate such as water, nitrogen ($N_2$), hydrogen sulfide, $C_{4+}$ mercaptans, amines, mixtures of amines, non-hydrocarbon non-volatiles (whether combustible or not) including refractory inorganics such as refractory oxygenates, inert gas (including inert gas mixtures), etc. In an embodiment, the first mixture comprises $\leq 10.0$ wt. % diluent. When the first mixture further comprises a molecular hydrogen diluent, the first mixture can have a molecular hydrogen to carbon (as all carbon atoms in the first mixture that are not bound to oxygen atoms, e.g., as can be determined by Nuclear Magnetic Resonance Spectroscopy) molar ratio in the range of from 0.0 to 5.0, e.g., 0.1 to 4.0, such as 1.0 to 3.0 or 1.0 to 2.0. Optionally, the first mixture has a hydrogen (all hydrogen atoms in the first mixture regardless of atomic or molecular form) to carbon (all carbon atoms in the first mixture regardless of atomic or molecular form) atomic ratio in the range of from 1.0 to 15.0, e.g., in the range of from 3.0 to 8.0.

Optionally, the first mixture comprises a total amount of non-combustible non-volatiles (e.g., ash; ASTM D-189), from all sources, $\leq 2.0$ parts per million weight (ppmw) based on the weight of the first mixture, e.g., $\leq 1.0$ ppmw. Optionally, the first mixture comprises a total amount of combustible non-volatiles (e.g., tar, asphaltenes, ASTM D-6560) in the first mixture, from all sources, $\leq 5$ wt. % based on the weight of the hydrocarbon in the first mixture, e.g., $\leq 1.0$ wt. %, such as $\leq 100.0$ ppmw or $\leq 10.0$ ppmw, provided the presence of the combustible non-volatiles does not result in $\geq 2.0$ ppmw (e.g., $\geq 1.0$ ppmw) based on the weight of the second mixture.

In one or more embodiments, the first mixture has one or more of the following properties: (i) at least 15.0 wt. % of the molecular hydrogen in the first mixture (based on the total weight of molecular hydrogen in the first mixture) is molecular hydrogen derived from the second mixture or one or more products thereof. In another embodiment, the first mixture comprises ≥50.0 ppmw sulfur based on the weight of the first mixture.

In one or more embodiments, the first mixture has the following composition (a) the first mixture comprises (i) ≥10.0 wt. % of hydrocarbon, e.g., ≥25.0 wt. % hydrocarbon and (ii) ≥1.0 wt. % molecular hydrogen, e.g., ≥15.0 wt. % molecular hydrogen, the weight percents being based on the weight of the first mixture and/or (b) the first mixture comprises (i) ≥0.10 mole % of hydrocarbon, e.g., in the range of 0.10 mole % to 90.0 mole % and (ii) ≥0.01 mole % of molecular hydrogen, e.g., in the range of 0.01 mole % to 90.0 mole %, the mole percents being per mole of the first mixture. Optionally, the hydrocarbon comprises (i) ≥25.0 wt. % methane (e.g., obtained from natural gas), e.g., ≥50.0 wt. % methane, such as ≥90.0 wt. % methane and/or (ii) ≥25.0 wt. % AGO, e.g., ≥50.0 wt. % AGO, such as ≥90.0 wt. % AGO; the weight percents being based on the weight of the first mixture's hydrocarbon.

FIG. 3 illustrates an embodiment where the first mixture is derived from one or more source materials 200, e.g., natural gas, petroleum, etc. The source materials can be upgraded in optional preparation stage 204. For example, when the source material is a natural gas comprising ≥10.0 wt. % methane and ≥1.0 wt. % ethane, stage 204 can be utilized for separating from the source material a utility composition comprising ≥10.0 wt. % ethane, e.g., ≥50.0 wt. % ethane, such as ≥90.0 wt. % ethane based on the weight of the utility composition. The utility composition can be conducted away from stage 204 via one or more conduits 2041. Optionally, at least a portion of the utility composition's ethane is utilized as a hydrogen donor for converting at least a portion of the second mixture's acetylene to ethylene (ethane donating hydrogen to the acetylene being also converted to ethylene).

When preparation stage 204 is not utilized, the first mixture can comprise (or consist essentially of, or even consist of) hydrocarbon obtained directly from source materials 200 such as natural gas or aromatic gas oil, e.g., with no intervening process steps. Following the optional preparation stage 204, the first mixture is conducted to the pyrolysis stage 206 wherein it is exposed to a temperature ≥1.20×10³° C. under thermal pyrolysis conditions, e.g., high-severity, thermal pyrolysis conditions, to convert at least a portion of the first mixture to the second mixture.

Another aspect of the invention is based in part on the discovery that the production of non-combustible, non-volatile molecules during pyrolysis can be lessened by dividing the first mixture into first and second portions before the pyrolysis. For example, the first mixture can be divided into first and second portions, where the first portion has (a) a hydrogen content of (i) <6.0 wt. % or (ii) in the range of 20.0 wt. % to 25.0 wt. % based on the weight of hydrocarbon in the first portion and/or (b) a non-combustible, non-volatiles content <2.0 ppm based on the weight of the first portion. The second portion has, e.g., (a) a hydrogen content ≥6.0 but <20.0 wt. % based on the weight of the second portion and/or (b) a non-combustible, non-volatile content ≥2.0 ppm based on the weight of the second portion.

This aspect of the invention can be carried out, e.g., by (a) exposing the first portion of the first mixture to a temperature ≥1.20×10³° C. in a first reaction region under substantially adiabatic thermal pyrolysis conditions, thereby reducing the first reaction region's temperature from a first temperature to a second temperature, the first temperature being ≥1.20×10³° C. and the second temperature being <1.20×10³° C.;

(b) exposing the second portion of the first mixture to a temperature <1.20×10³° C. in the first reaction region under substantially adiabatic thermal pyrolysis conditions, thereby reducing the first reaction region's temperature from the second temperature to a third temperature;
(c) conducting away a second mixture comprising ≥1.0 wt. % of unsaturates, e.g., $C_2$ unsaturates, based on the weight of the second mixture; and
(d) increasing the first region's temperature to a fourth temperature, the fourth temperature being ≥the first temperature, e.g., by combusting a fourth mixture in a second region; the second region being at least partially coextensive with the first region.

Optionally, steps a-d are carried out in a regenerative, reverse-flow thermal pyrolysis reactor. Should the second mixture comprise acetylene, hydrogen transfer can be utilized, e.g., as described in connection with other embodiments, for converting at least a portion of the acetylene to ethylene.

The second mixture as produced in certain embodiments will now be described in more detail.

Second and Third Mixtures

The second mixture generally comprises ≥1.0 wt. % of unsaturates and ≥1.0 wt. % of combustible non-volatiles, based on the weight of the second mixture. Optionally, the second mixture further comprises one or more of hydrogen, methane, ethane, or diluent, and optionally further comprises benzene, paraffin (iso-, cyclo-, and/or normal) having ≥3 carbon atoms, etc.

In an embodiment, ≥90.0 wt. %, e.g., ≥95.0 wt. %, such as ≥99.0 wt. % of the second mixture's combustible non-volatiles remain in the regenerative, reverse-flow pyrolysis reactor, e.g., as a deposit in the channels of the first and/or second reactor, the weight percents being based on the weight of the combustible non-volatiles in the second mixture.

At least a portion of the second mixture, e.g., a vapor-phase portion which comprises acetylene, ethylene, hydrogen, and saturated hydrocarbon, is conducted away from the pyrolysis stage to an optional upgrading stage 208. A combustible non-volatile portion of the second mixture can remain in the stage 206, e.g., as a deposit in the pyrolysis reactor. Upgrading stage 208 can be utilized, e.g., for deriving a third mixture from the second mixture, the third mixture comprising at least a portion of the second mixture's acetylene.

In an embodiment, the third mixture is derived from the second mixture in one or more upgrading/treatment stages, e.g., by separating from the second mixture one or more of hydrogen, methane, and/or combustible non-volatiles. In another embodiment, the third mixture comprises, consists essentially of, or consists of the second mixture, e.g., that part of the second mixture which is in the vapor phase at the downstream end of a regenerative, reverse-flow pyrolysis reactor.

Fourth and Fifth Mixtures

The fourth mixture comprises first and second reactants. The first reactant comprises fuel and the second reactant comprises oxidant. As shown in FIG. 3, the first reactant can be derived from at least one source material 300, e.g., natural gas, aromatic gas oil, other hydrocarbon, etc., including fractions, products, or byproducts thereof. Optionally, the first reactant and first mixture are derived from substantially the same source material. The second reactant can comprise, e.g., oxygen, etc., and can be derived from a source material 301, such as air. Optionally, the first reactant's source material 300 is upgraded in a second preparation stage 302 upstream of conduit 305. Stage 302 can optionally include one or more of separation, conversion, addition of recycled portions of the second and/or fifth mixtures, etc. Optionally, the second reactant's source material 301 is upgraded in a second preparation stage 303 upstream of conduit 3051. Stage 303 can optionally include one or more of separation, conversion, addition of recycled portions of the second and/or fifth mixtures, etc.

The fuel and oxidant can be the same as those disclosed in U.S. Pat. No. 7,943,808. Optionally, the fuel is derived from, comprises, consists essentially of or consists of one or more of hydrogen, CO, methane, methane containing streams such as coal bed methane, biogas, associated gas, natural gas, and mixtures or components thereof, etc. Exothermically reacting the first reactant's fuel component and the second reactant's oxidant component provides at least a portion of the heat utilized by the pyrolysis, e.g., ≥50%, such as ≥75%, or ≥95% of the heat utilized by the pyrolysis. Additional heat, when needed, can be provided to the regenerative, reverse-flow pyrolysis reactor by, e.g., a burner or furnace, e.g., a furnace external to the reactor, but in thermal communication therewith. The first and second reactants mix within the regenerative, reverse-flow pyrolysis reactor to produce the fourth mixture, the fuel and oxidant then reacting, e.g., by an oxidation reaction such as combustion, as the fourth mixture traverses at least a portion of the pyrolysis reactor. The first reactant comprises fuel, e.g., molecular hydrogen, synthesis gas (mixtures of CO and $H_2$), or hydrocarbon, such as ≥10.0 wt. % hydrocarbon (including mixtures thereof), or ≥50.0 wt. % hydrocarbon, or ≥90.0 wt. % hydrocarbon based on the weight of the first reactant. The second reactant comprises oxidant, e.g., molecular oxygen.

The amount of oxidant in the second reactant and the relative amounts of first and second reactants utilized to produce the fourth mixture can be specified in terms of the amount of oxidant in the second reactant needed for oxidizing combustible non-volatiles in the reactor system ("X") and the amount needed for the substantially stoichiometric oxidation of the first reactant's fuel component ("Y"). In an embodiment, the total amount of oxidant in the fourth mixture is Z(X+Y), wherein Z is in the range of 0.8 to 10.0, e.g., in the range of 1.0 to 3.0, and the amounts X and Y are on a molar basis. When Z>1.0, the excess oxidant can be utilized, e.g., for moderating the reaction temperature during the oxidation step as disclosed in U.S. Pat. No. 7,943,808, and/or for conveying heat within the reactor system.

The fourth mixture is generally produced in a mixing region, the mixing region being located downstream of the first reactor's channels. The fourth mixture is defined as the combination of the first reactant and second reactant. However, at the point at which these streams combine, the combined stream optionally includes species resulting from the oxidation of combustible non-volatiles located in the first reactor's channels. Optionally, the combined stream further comprises species resulting from reaction of the first and second reactants in one or more of the first reactor's channels, or locations upstream thereof, as a result of comingling of the first and second reactants. Generally, the amount of comingling is small, as disclosed in U.S. Pat. No. 7,943,808. It can be beneficial for the amount of oxidant in the fourth mixture to exceed that needed to oxidize substantially all of the fourth mixture's fuel component, e.g., for (i) oxidizing combustible non-volatiles located in regions of the reactor system downstream of the first reactor's channels, (ii) moderating the temperature during the oxidation of the fourth mixture's fuel component, and/or (iii) transferring heat within regions of the reactor system downstream of the mixing region. The desired amount of excess oxygen can be provided by increasing the relative amount of oxidant in the second reactant and/or by increasing the relative amount of second reactant in the fourth mixture.

Optionally, the fourth mixture further comprises diluent, e.g., ≥1.0 wt. % of diluent based on the weight of the fourth mixture. Suitable diluents (which can be a diluent mixture) include one or more of, e.g., oxygenate (water, carbon dioxide, etc.), non-combustible species such as molecular nitrogen ($N_2$), and fuel impurities such as hydrogen sulfide. In an embodiment, the fourth mixture comprises ≤96.0 wt. % diluent, e.g., in the range of 50.0 wt. % to 95.0 wt. % diluent, based on the weight of the fourth mixture. In an embodiment, diluent is provided to the fourth mixture as a component of the second reactant. For example, the second reactant can comprise 60.0 mole % to 95.0 mole % diluent and 5.0 mole % to 30.0 mole % oxidant per mole of the second reactant, such as when the second reactant is air. Optionally, the second reactant has a mass ratio of diluent to oxidant in the range of 0.5 to 20.0, e.g., in the range of 4.0 to 12.0. It can be beneficial for the second reactant (and fourth mixture) to further comprise diluent, e.g., for moderating the temperature during the oxidation of the fourth mixture's fuel component and/or transferring heat within the reactor system.

In one or more embodiments, the first reactant comprises ≥90.0 wt. % methane based on the weight of the first reactant and the second reactant comprises ≥90.0 wt. % air based on the weight of the second reactant. When the second reactant comprises ≥90.0 wt. % air based on the weight of the second reactant, a fourth mixture produced from these can comprise, e.g., ≥1.0 wt. % molecular oxygen, e.g., in the range of 5.0 wt. % to 25.0 wt. %, such as 7.0 wt. % to 15.0 wt. %; ≥0.1 wt. % fuel, e.g., in the range of 0.8 wt. % to 20.0 wt. %, the weight percents being based on the weight of the fourth mixture, with the balance of the fourth mixture being molecular nitrogen diluent, e.g., ≥50.0 wt. % diluent, such as in the range of 60.0 wt. % to 94.2 wt. % diluent based on the weight of the fourth mixture.

The fifth mixture generally comprises (i) products derived from the exothermic reaction of the fourth mixture's fuel and oxidant with each other and with the combustible non-volatiles within the reactor, optionally (ii) diluent, when diluent is present in the fourth mixture, and/or (iii) unreacted fuel and oxidant. When the exothermic reaction of the fuel and oxidant involves hydrocarbon combustion, or when a diluent is present in the fourth mixture (such as $N_2$ or $H_2S$), the fifth mixture can comprise carbon dioxide, and can further comprise sulfur oxides, nitrogen oxides, etc.

A continuous process for deriving (a) the second mixture from the first mixture and (b) the fifth mixture from the fourth mixture in a regenerative, reverse-flow reactor system will now be described in more detail. Although the process is described in terms of sequential pyrolysis and oxidation steps operated in a particular regenerative, reverse-flow thermal pyrolysis reactor, the invention in not limited thereto, and this description is not meant to foreclose other embodiments within the broader scope of the invention.

Continuous Process for Producing the Second Mixture

Figure 4:
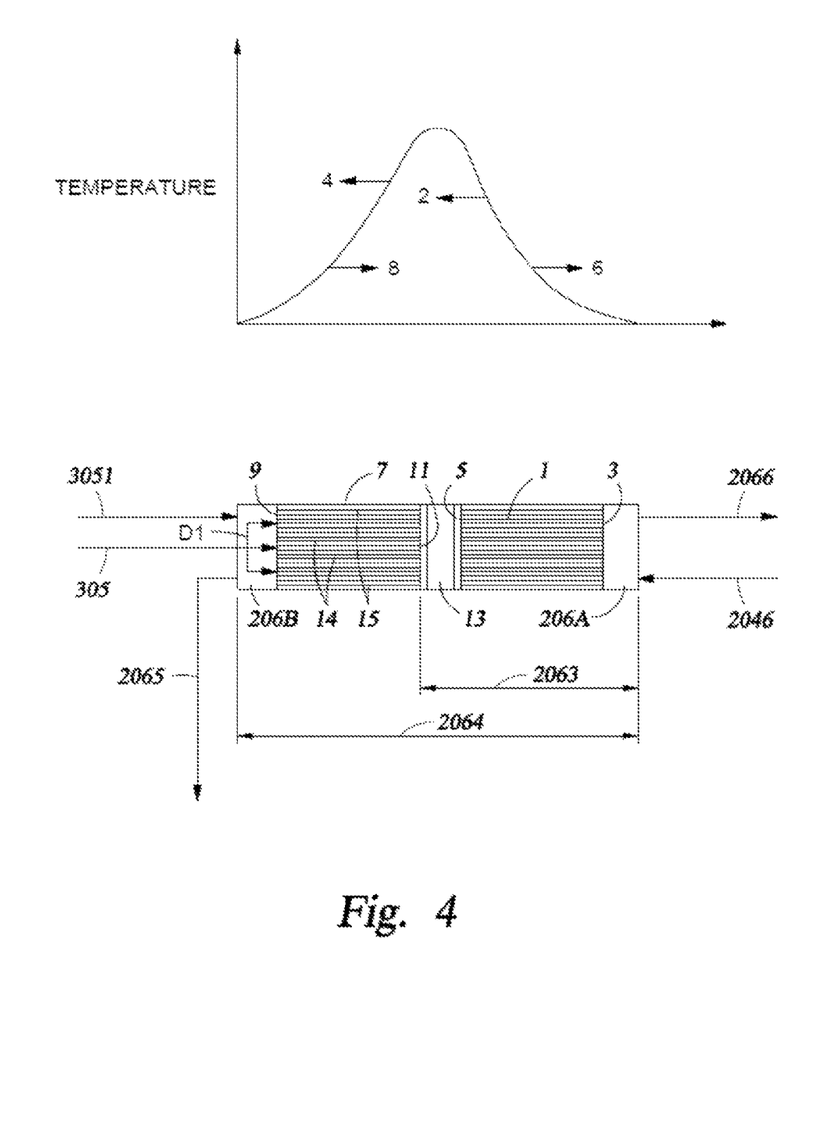
FIG. 4 schematically shows a pyrolysis reactor that can be used in the embodiment of FIG. 3.
Figure 5:
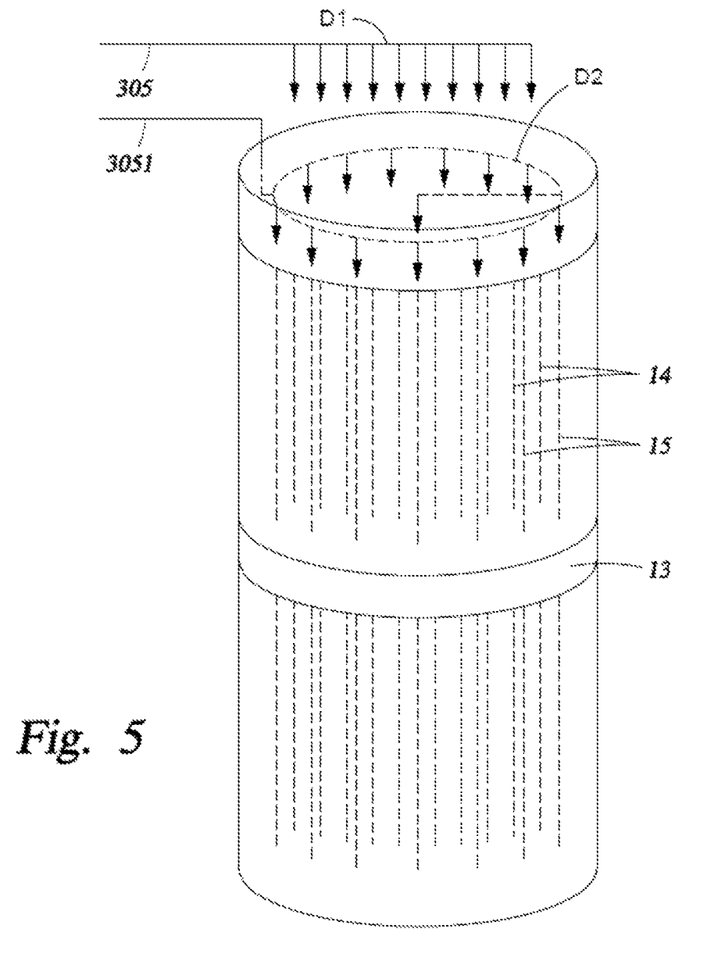
FIGS. 5 and 5A illustrate an alternative embodiment of the pyrolysis reactor and a flow-distributor that can be utilized therein.
Figure 5A:
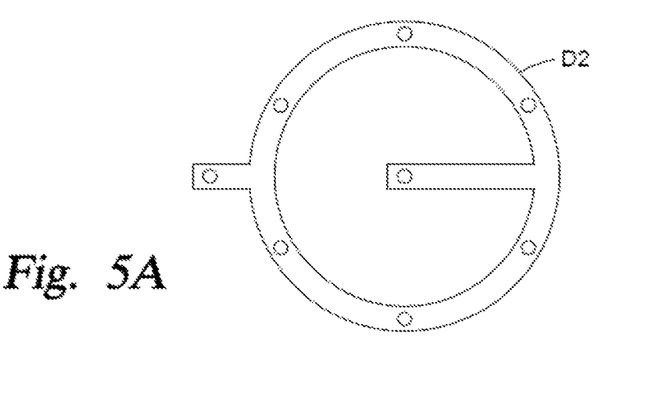

Referring to FIG. 3, the process comprises oxidation and pyrolysis steps carried out continuously or semi-continuously in pyrolysis stage 206, wherein stage 206 utilizes the regenerative, reverse-flow thermal pyrolysis reactor system illustrated schematically in FIGS. 4, 5, and 5A. As shown in the figures, stage 206 comprises two reactors: a first (recuperator/quenching) reactor 7 and a second (pyrolysis) reactor 1, the first reactor 7 comprising at least one first channel 14 and at least one second channel 15. As shown in FIG. 4, the exothermic reaction region 2063 can be located, e.g., between a first point proximate to the downstream end 11 of first reactor 7 and a second point proximate to the downstream end 3 of second reactor 1; "downstream" in this case being with respect to the average flow of the fourth mixture. The pyrolysis region 2064 can be located, e.g., between a first point proximate to the upstream end 3 of the second reactor 1 and a second point proximate to the downstream end 9 of first reactor 7, "upstream" and "downstream" now being with respect to the average flow of the first mixture. It should be appreciated that the invention can be practiced without precisely defining (a) the boundaries of regions 2063 and 2064. Although region 2063 (the exothermic reaction region) is at least partially coextensive with pyrolysis region 2064, the upstream end of region 2063 ("upstream" with respect to the average flow of the fourth mixture) is generally proximate to the location where sufficient fuel and oxidant combine to produce an exothermic reaction. The downstream (with respect to the average flow of the first mixture) end of region 2063 is generally proximate to the downstream end of second reactor 1 as shown in FIG. 4, though this is not required, and in at least one embodiment the downstream end of region 2063 is located further downstream, e.g., in conduit 2066. In at least one of the embodiments represented by FIG. 1, the upstream end of pyrolysis region 2064 is proximate to the upstream end 3 of the second reactor 1. The downstream end of pyrolysis region 2064 is proximate to the downstream end 9 of the first reactor 7. Since the quenching heats the first reactor 7, the oxidation step optionally includes cooling the first reactor, e.g., to shift the tail of the temperature profile (indicated by trend-line 8) away from end 9 of the first reactor 7, as illustrated schematically in FIG. 4. The reactors 1 and 7 can be of the same shape and size, but this is not required. For example, the reactors can each be in the form of a honeycomb monolith of substantially cylindrical cross-section.

It is understood that flow control means (e.g., one or more of valves, rotating reactor beds, check valves, louvers, flow restrictors, timing systems, etc.) can be used to control gas flow, actuation, timing, and to alternate physical beds between the flow systems for the first, second, fourth, and fifth mixtures, and the optional purge gas when used. For example, stage 206 can further comprise means for conveying first reactant (via conduit 305) and second reactant (via conduit 3051) into the appropriate channels in the first reactor. Such means can include, e.g., one or more of plenums, valves, vanes, spargers and/or distributors. Suitable spargers, distributers, etc. are disclosed in U.S. Pat. No. 7,815,873; which is incorporated by reference herein in its entirety. Although the invention is compatible with the use of conventional spargers, distributors, plenums, etc, is stage 206, the invention is not limited thereto. The pyrolysis and oxidation steps will now be described in more detail.

Pyrolysis Step

During the pyrolysis step, the first mixture is conducted to the first region (the pyrolysis region) 2064 of the regenerative, reverse-flow pyrolysis reactor via at least one conduit 2046. The second mixture, derived from the first mixture by the pyrolysis is conducted away from region 2064 via at least one conduit 2065. The reactor optionally includes means for directing the first mixture from conduit 2046 into the channels of the second reactor 1, e.g., plenum 206A and means (such as plenum 206B) for directing at least a portion of the second mixture, e.g., the portion in the vapor phase, to conduit 2065.

In the illustrative embodiment, regions 2063 and 2064 are at least partially coextensive as shown in FIG. 3. Region 2063 encompasses at least the second reactor. Region 2064 encompasses at least a portion of each of the first and second reactors. At least a portion of the heat produced in region 2063 during the exothermic reaction of the fourth mixture during the first and second intervals of the oxidation step is used to provide at least a portion of the heat utilized in region 2064 for the endothermic pyrolysis step. Optionally, a major amount (e.g., >50%) of the heat abstraction occurs in the portion of region 2064 that is coextensive with region 2063.

At least a portion of the second mixture's acetylene is reacted catalytically in stage 210 with at least one hydrogen donor to convert the acetylene to, e.g., ethylene. For example, a third mixture can be derived from at least a portion of the second mixture in optional upgrading stage 208, the third mixture comprising at least a portion of the second mixture's acetylene. The third mixture can be conducted via at least one conduit 2086 to stage 210, for converting at least a portion of the third mixture's acetylene to a first product comprising ethylene. The first product can be conducted away via conduit 2101. The hydrogen donor is conducted to stage 210 via one or more conduits 2102.

In one embodiment, stage 208 includes upgrading means, e.g., means for removing from the second mixture one or more of hydrocarbon (such as saturated hydrocarbon and/or those containing one or more heteroatoms), diluent, non-volatiles, and hydrogen, etc. For example, at least a portion of any light-gas in the second mixture (e.g., one or more of hydrogen, light saturated hydrocarbon such as methane, carbon dioxide, hydrogen sulfide, etc.) can be removed in stage 208. Optionally, the removed light gas can be used, e.g., to adjust the stoichiometry of the first or fourth mixtures (e.g., by increasing the hydrogen and/or diluent content, etc.), as a stripping medium (e.g., for upgrading one or more sources from which the first mixture is derived, such as by stripping upstream of stage 206, e.g., in stage 204), etc. Separated molecular hydrogen can be conducted away, e.g., for recycle to produce the first or fourth mixtures. Stage 208 can also include means for removing at least a portion of any water present in the second mixture, e.g., by one or more of a methanol treatment, such as those described in Belgian Patent No. 722,895, adsorption, extraction by diethylene glycol, etc. Stage 208 can also include, e.g., means for cooling and then compressing the second mixture conducted away from stage 206. Should the second mixture comprise acid gases (e.g., $CO_2$ and/or $H_2S$), these can be removed, e.g., downstream of the compression—a desirable location since the gas volume has been reduced significantly during compression. Molecular hydrogen, saturated hydrocarbon, diluent, etc., separated from $C_2$ unsaturates in upgrading stage 208 can be recycled, e.g., by combining such separated species with one or more of the first mixture's source materials, e.g., in preparation stage 204.

Stage 208 can be utilized for producing a third mixture comprising acetylene, e.g., by contacting the second mixture with a polar utility fluid, such as one or more of furfural, phenol, n-methyl-2-pyrrolidone, methanol, acetone or tetrahydrofuran. Suitable utility fluids are disclosed in U.S. Pat. Nos. 3,093,697; 3,617,495; 4,274,841; and 7,045,670, which are incorporated by reference herein in their entirety. In an embodiment, the third mixture comprises an extract, the extract comprising at least a portion of the utility fluid and ≥50.0 wt. %, e.g., ≥75.0 wt. %, such as ≥90.0 wt. % of the second mixture's acetylene, based on the total weight of acetylene in the second mixture. A raffinate comprising non-acetylene species in the second mixture, e.g., molecular hydrogen and/or methane, can be conducted away from stage 204. Methane and/or molecular hydrogen obtained from the raffinate can be utilized, e.g., to produce the first and/or fifth mixtures. The pyrolysis process conditions will now be described in more detail. In another embodiment, the third mixture comprises ≤1.0 wt. % of the utility fluid, e.g., ≤0.1 wt. %, such as ≤0.01 wt. % based on the weight of the third mixture, e.g., where stage 208 further comprises separating at least a portion of the extract's acetylene from the utility fluid to produce the third mixture.

In an embodiment, the pyrolysis is conducted under high-severity thermal pyrolysis conditions, e.g., by exposing the first mixture to a temperature in the range of about $1.40 \times 10^{3}$° C. to about $2.30 \times 10^{3}$° C., e.g., in the range of about $1.45 \times 10^{3}$° C. to about $1.80 \times 10^{3}$° C. at a residence time ≤about 0.3 seconds, e.g., ≤0.05 seconds. Optionally, the residence time is ≤0.05 seconds, such as ≤0.02 seconds. Optionally, ≥25.0 wt. % (such as of the ≥50.0 wt. % or ≥75.0 wt. %) of the first mixture achieves a peak pyrolysis gas temperature ≥$1.40 \times 10^{3}$° C., e.g., in the range of about $1.50 \times 10^{3}$° C. to about $1.675 \times 10^{3}$° C., based on the weight of the first mixture.

In an embodiment, the pyrolysis is conducted for a time duration ($t_1$) sufficient for exposing ≥50.0 wt. %, e.g., ≥75.0 wt. %, such as ≥90.0 wt. % of the first mixture (based on the weight of the first mixture) to pyrolysis conditions for a residence time ≤about 0.3 seconds, e.g., ≤0.05 seconds. In an embodiment, $t_1$ is ≤10.0 seconds, e.g., ≤5.0 seconds, such as ≤1.0 seconds. Optionally, $t_1$ is in the range of $1.0 \times 10^{-3}$ seconds to 10.0 seconds.

In an embodiment, the pyrolysis step includes one or more of the following conditions: the first mixture achieves a peak pyrolysis gas temperature ≥$1.40 \times 10^{3}$° C., e.g., in the range of $1.45 \times 10^{3}$° C. to $2.20 \times 10^{3}$° C., such as, $1.50 \times 10^{3}$° C. to $1.90 \times 10^{3}$° C., or $1.60 \times 10^{3}$° C. to $1.70 \times 10^{3}$° C.; a total pressure ≥1.0 bar (absolute), e.g., in the range of 1.0 bar to about 15 bar, such as in the range of 2.0 bar to 10.0 bar; a residence time (during high severity conditions) ≤0.1 seconds, e.g., ≤$5.0 \times 10^{-2}$ seconds, such as ≤$5.0 \times 10^{-3}$ seconds and/or a $t_1$ in the range of $1.0 \times 10^{-3}$ seconds to 10.0 seconds.

Oxidation Step

During the oxidation step, the first reactant is conducted through at least one conduit 305 and optionally to at least one first distributor (D1), wherein D1 directs the flow of the first reactant into first channel 14 within first reactor 7. The second reactant is conducted through at least one conduit 3051 and optionally to at least one second distributor (D2), wherein D2 directs the flow of the second reactant to second channel 15 within first reactor 7. D2 can comprise plenum 206B as shown in FIG. 4. In another embodiment, D2 comprises at least one oxidant grid, the oxidant grid, e.g., being used alone or in combination with plenum 206B. When the regenerative, reverse-flow pyrolysis is cylindrically symmetric, the oxidant grid's orifices can be located in a circular pattern around a central orifice as illustrated in FIGS. 5 and 5A. The orifice shown to the far left in FIG. 5A can be utilized for connecting the grid to conduit 3051.

The first and second reactants are combined in mixer-distributor zone 13 to produce the fourth mixture (for the exothermic reaction) in proximity to the downstream end of first reactor 7, which in this embodiment defines the upstream end of an exothermic reaction region 2063. For the description of the oxidation step, upstream and downstream are defined with respect to the average flow of the fourth mixture, and components and products thereof. A fifth mixture is directed by plenum 206A to at least one conduit 2066, and conducted away from the regenerative, reverse-flow pyrolysis reactor. The fifth mixture comprises (i) compositions resulting from the reaction of the fourth mixture's fuel and oxidant, (ii) any fourth mixture that is not consumed in the reaction, and (iii) compositions resulting from the oxidation of combustible non-volatiles, e.g., those deposited in the reactor system during preceding pyrolysis step(s).

In this embodiment, the total duration of an oxidation step $t_2$ is greater than or equal to the time needed for the second reactor to abstract sufficient heat from the oxidation to accomplish the pyrolysis step. In other words, the oxidation step is conducted for a time duration greater than or equal to a time sufficient to displace the peak of the temperature profile toward the second reactor sufficient to heat the pyrolysis region 2064 for exposing the first mixture to a temperature ≥$1.20 \times 10^{3}$° C. during the pyrolysis step. The value of $t_2$ depends on factors such as the geometry of the reactors utilized in stage 206, the heat transfer characteristics of the reactors and the materials from which the reactors are made, and the amount of heat needed by the pyrolysis step. Optionally, $t_2$ is in the range of $1.0 \times 10^{-3}$ seconds to 10.0 seconds. In an embodiment, $t_2$ is greater than or equal to the time needed to heat the pyrolysis region 2063 to a temperature sufficient for exposing ≥50.0 wt. % of the first mixture, e.g., ≥75.0 wt. %, such as ≥90.0 wt. % to a temperature ≥$1.20 \times 10^{3}$° C. during the pyrolysis step; the weight percents being based on the weight of the first mixture. In an embodiment, $t_2$ is ≤10.0 seconds, e.g., ≤5.0 seconds, such as ≤1.0 seconds.

During continuous operation of the reactor system and after equilibrium is established, the total amount of heat added to the reactor system during an oxidation step is optionally ≤5.0 times the amount heat required (a) to sustain the pyrolysis reaction for endothermically driving the second mixture from the pyrolysis portion of the first mixture and (b) for heat losses from the system, e.g., by thermal radiation losses, thermal conduction losses (e.g., through reactor walls) and/or convection losses (e.g., heat carried away with the second mixture), e.g., ≤2.0 times, such as ≤1.1 times. The total amount of heat stored in the reactor system is generally much more than the minimum amount of heat needed for the pyrolysis step.

In an embodiment, the exothermic reaction of the fuel and oxidant components of the fourth mixture includes combustion, the combustion conditions including a temperature ≥$1.40 \times 10^{3}$° C., e.g., ≥$1.50 \times 10^{3}$° C. such as ≥$1.60 \times 10^{3}$° C., e.g., in the range of $1.90 \times 10^{3}$° C. to $2.20 \times 10^{3}$° C., and a pressure ≥1.0 bar (absolute), e.g., in the range of 1.0 bar to 15.0 bar, such as 2.0 bar to 5.0 bar. Optionally, the oxidation step oxidizes ≥97.0 wt. % the fourth mixture's fuel component, e.g., ≥98.0 wt. %, such as, e.g., ≥99.0 wt. %, based on the weight of the fourth mixture's fuel component. Optionally, diluent such as nitrogen that may be present in the fourth mixture is not oxidized to a significant extent.

After at least a portion of the fifth mixture is conducted away from region 2063, the first mixture is again conducted to region 2064, and the process repeats in sequence—exothermically reacting the fourth mixture's fuel and oxidant components to heat the reactor and then utilizing at least a portion of the heat for pyrolysing the first mixture. At the conclusion of the oxidation step, optional upgrading stage 308 can be used, e.g., to separate from the fifth mixture species (e.g., diluent) that may be useful in other stages of the process.

The process can be operated sequentially, e.g., continuously, semi-continuously, or even in batch mode. In an embodiment, stage 206 comprises a plurality of pyrolysis reactors operating, e.g., in series, parallel, or a combination thereof, with at least one pyrolysis reactor having (i) pyrolysis step(s) and (ii) oxidation step(s) having the described first and second intervals. When stage 206 comprises a plurality of pyrolysis reactors, the sequence of oxidation steps and pyrolysis steps in each reactor can be out of phase, e.g., to provide a continuous flow of second mixture from the process. For example, the second mixture can be obtained from a first reactor in stage 206 undergoing a pyrolysis step while a second reactor is undergoing an oxidation step in a first period, and then in a second period the second mixture is obtained from the second reactor undergoing a pyrolysis step while the first reactor is undergoing an oxidation step.

Optionally, the process further includes one or more of the following: treating/upgrading stage 308 for treating and/or upgrading the fifth mixture downstream of conduit 2066; one or more conduits 3001 for adding to the first reactant's source material 300 one or more of diluent, molecular hydrogen, and/or light saturated hydrocarbon; one or more conduits 3004 for adding to the second reactant's source material 301 supplemental oxidant or diluent; one or more conduits 2043 for adding to the first mixture's source material one or more of molecular hydrogen, hydrocarbon, e.g., light saturated hydrocarbon such as methane, or diluent; one or more conduits 2041 for conducting away heteroatom species such as hydrogen sulfide, non-volatiles, or other species separated from the first mixture's source material; one or more conduits 3081 for conducting away from upgrading stage 308 one or more of non-oxidized hydrocarbon diluent, heteroatom species (such as $NO_x$, $SO_x$, $CO_2$, $N_2$, sulfuric acid, etc.); one or more conduits 2082 for conducting away from stage 208 one or more of molecular hydrogen, light saturated hydrocarbon, non-volatiles, or heteroatom species such as hydrogen sulfide; one or more conduits 2083 for conducting a utility fluid to stage 208, e.g., for extracting at least a portion of the second mixture's acetylene; or one or more conduits (not shown) for adding to the second mixture one or more of (i) hydrogen, (ii) methane, ethane, and/or other light saturated hydrocarbon; or (iii) ethylene. Optionally, stages 208 and 308 can be utilized to provide streams for adjusting the composition of the first-fifth mixtures.

For example, when it is desired to (a) increase the relative amount of one or more of hydrocarbon (e.g., methane) and/or hydrogen in the first reactant 305 over that of its source material 300 or (b) increase the relative amount of oxidant (e.g., oxygen and/or ozone) in the second reactant 3051 over that of its source material 301, this can be done as follows:
(a) Hydrocarbon can be added, the hydrocarbon being obtained, e.g., from (i) external sources and/or (ii) sources within the process, such as from optional stages 308 and 208.
(b) Oxidant can be added, the added oxidant being obtained from (i) external sources and/or (ii) sources within the process such as from optional stage 308. When the source material is air, the air can be obtained from a blower or compressor, for example.

When it is desired to increase the amount of one or more of molecular hydrogen, hydrocarbon, or diluent in the first mixture, these can be added (e.g., in stage 204) as follows:
(i) Molecular hydrogen can be added via conduit 2043, with the added hydrogen obtained, e.g., from one or more of (a) from optional stage 208, (b) from molecular hydrogen separated from the first product, or (c) from an external source.
(ii) Hydrocarbon can be added via conduit 2043, the hydrocarbon being obtained from e.g., optional stages 308 and 208, from hydrocarbon separated from the first product, or from an external source.
(iii) Diluent (such as oxygenate) can be added via conduit 2043, the diluent being obtained, e.g., (a) from optional stage 308, (b) from the first product, (c) from the second mixture, and/or (d) from a source external to the process.

The second mixture (conduit 2065) or a third mixture containing at least a portion of the second mixture's acetylene (conduit 2081) is conducted to stage 210 for catalytically transferring hydrogen to at least a portion of the acetylene. The hydrogen-transfer step will now be described in more detail.

Hydrogen Transfer

In an embodiment, hydrogen is catalytically transferred from a hydrogen donor to acetylene in stage 210, the acetylene being obtained from (i) the second mixture or (ii) a third mixture derived from the second mixture, the third mixture containing, e.g., ≥10.0 wt. %, e.g., ≥50.0 wt. %, such as ≥90.0 wt. % of the second mixture's acetylene, based on the weight of the second mixture's acetylene. The hydrogen donor is conducted to stage 210 via conduit 2102. At least a portion of the hydrogen-transfer product is conducted away from the stage 210 via conduit 2101. Generally, the hydrogen-transfer reaction results in the conversion to monoolefin of ≥25.0% of the acetylene in the feed to the hydrogen-transfer stage on a mole basis, e.g., ≥50.0%, such as ≥75.0%.

The hydrogen donor can be, e.g., paraffin containing 2 or more carbon atoms, including mixtures comprising such paraffins. The paraffin can be one or more of normal paraffin, iso-paraffin, cyclo-paraffin, etc., including derivatives thereof. Optionally, the hydrogen donor comprises ≥50.0 wt. %, e.g., ≥75.0 wt. %, such as ≥95.0 wt. % of normal paraffin and/or iso-paraffin, based on the weight of the hydrogen donor. Suitable paraffins include ethane and/or propane. The amount of hydrogen donor present in stage 210 during the hydrogen transfer can be, e.g., in the range of from 0.5 to 20.0, such as 1.0 to 10.0, or 2.0 to 10.0 moles per mole of acetylene present in stage 210 during the hydrogen transfer. In an embodiment (not shown), the hydrogen donor comprises ethane, wherein ≥1.0 wt. %, e.g., ≥2.0 wt. %, e.g., ≥5.0 wt. % of the hydrogen donor's ethane is obtained from the second mixture based on the weight of the hydrogen donor's ethane. In this embodiment, at least a portion of the hydrogen donor is conveyed to stage 210 via conduits 2065 or 2081.

Diluent can be present in the hydrogen-transfer reaction, e.g., to moderate reactant and product partial pressures. When at least a portion of the diluent comprises one or more species produced in the pyrolysis and retained in the third mixture, it can be conveyed to the stage 210 with the third mixture (e.g., via conduit 2081). In another embodiment (not shown) the diluent comprises at least a portion of the non-acetylene components of the second mixture which are in the vapor-phase at the downstream end of stage 206, the diluent being conveyed to stage 210 with the second mixture's acetylene, e.g., with no intervening process steps via conduit 2065. Optionally, at least a portion of the diluent is (i) conveyed to stage 210 with the hydrogen donor via conduit 2102 or (ii) conveyed via a diluent conduit (not shown).

In an embodiment, the diluent comprises, e.g., methane and/or one or more of the diluents specified for the first mixture. In an embodiment, the diluent constitutes ≤50.0 wt. %, e.g., ≤25.0 wt. %, such as ≤5.0 wt. % of the combined weight of acetylene+hydrogen donor+diluent present in stage 210 during the hydrogen transfer reaction. In an embodiment, the diluent comprises ≥50.0 wt. % of (i) methane and/or (ii) molecular hydrogen based on the weight of the diluent. Optionally, the diluent comprises ≥1.0 wt. % of olefin, e.g., in the range of 1.0 wt. % to 10.0 wt. % ethylene based on the weight of the diluent, such as in the range of 1.0 wt. % to 10.0 wt. % ethylene based on the weight of the diluent. When the diluent comprises molecular hydrogen, the amount of molecular hydrogen (molar basis) is optionally ≤10.0 times the total amount of hydrocarbon (hydrogen-donor hydrocarbon+diluent hydrocarbon, molar basis) present during the hydrogen transfer.

The catalyst utilized for the hydrogen transfer can be the same as those specified in U.S. Pat. No. 5,585,530. Suitable catalysts include those comprising one or more catalytic metal, e.g., one or more of (i) noble metal, e.g., one or more of rhenium, ruthenium, rhodium, palladium, silver, osmium, iridium, platinum, or gold; (ii) one or more metals selected from Group VI of the Periodic Table, e.g., chromium and/or molybdenum; or (iii) one or more non-noble metals selected from Group VIII of the Periodic Table, e.g., one or more of iron, nickel, or cobalt; including oxide and sulfide derivatives of any of the foregoing (i), (ii), or (iii) metals or metal mixtures. In an embodiment, the hydrogen-transfer catalyst comprises ≥0.5 wt. % of one or more of the foregoing catalytic metals, e.g., in the range of 1.0 wt. % to 15.0 wt. % catalytic metal and ≥99.5 wt. % of at least one support based on the weight of the catalyst, the support comprising e.g., alumina, zirconia and/or alkaline earth oxides, especially those stabilized for use at high temperatures. In an embodiment, the catalyst comprises ≥5.0 wt. % of (i) chromia or (ii) a combination of platinum and tin, and ≤95.0 wt. % of an alumina support, the weight percents being based on the weight of the catalyst. Optionally, the chromia and/or platinum-tin are in admixture with a platinum group metal, and optionally doped with alkali, wherein the alkali can be, e.g., potassium and/or cesium.

Preferably, the hydrogen-transfer catalyst has a relatively high activity for paraffin dehydrogenation to initiate the reaction and a relatively low activity for olefin hydrogenation and light alkane hydrogenolysis. One preferred catalyst includes one of more metals selected from Group VIII of the Periodic Table, the metal being supported on a refractory oxide support (such as silica, zirconia, or alumina) The metal can be platinum and/or palladium, for example. Optionally, the Group VIII metal is modified by addition of one or more Group IB metals, e.g., one or more of copper, silver, or gold. While not wishing to be bound by any theory or model, it is believed that the addition of one or more Group IB metal reduces coking and reduces the binding energy of acetylene relative of propane and propylene. Optionally, the atomic ratio of Group IB metal:Group VIII metal is in the range of about 0.01 to 0.25. In another embodiment, the Group IB metal can be replaced by one or more of tin, indium, gallium, or germanium. While not wishing to be bound by any theory or model, it is believed that the use of these metals can be significantly lessened hydrogenolysis activity without significantly decreasing dehydrogenation activity. Optionally, the catalyst further comprises low levels (≤0.1 wt. % based on the weight of the catalyst) of one or more alkali or alkali earth metals such as sodium, potassium, calcium, or magnesium. It is believed that these inhibit undesirable conversion of acetylene to ethane.

In another embodiment, the hydrogen-transfer catalyst comprises transition-metal carbides, nitrides, phosphides, silicides, borides, etc. It is believed that these materials combine high activity for light paraffin activation, resistance to coking, and high thermal stability. The metal carbide or nitride can also be promoted with minor amounts of alkali or alkali earth metals to reduce hydrogenation activity, if desired.

Suitable homogenous molecular catalysts can be based on Group VIII metal centers coordinated by one or more ligands containing nitrogen or phosphorous, e.g., those containing one or more "pincer metal hydride" complexes (and/or organometallic derivatives thereof). It is believed that these catalysts have thermal stability at temperatures ≥150° C. Such catalysts can comprise, e.g., ≥1.0 wt. % iridium, based on the weight of the catalyst.

The catalytic hydrogen-transfer reaction can be carried out with the reactants in the liquid phase, gas phase, or a combination thereof. The hydrogen-transfer catalyst can be in the form of a liquid, solid, slurry, or a combination thereof. The process conditions utilized for the hydrogen transfer can be the same as those specified in U.S. Pat. No. 5,585,530. For example, the total pressure can be in the range 0.3 bar (absolute) to 20.0 bar (absolute), e.g., in the range of 0.5 bar (absolute) to 10.0 bar (absolute), such as in the range 1.0 bar (absolute) to 5.0 bar (absolute); the partial pressure of hydrogen donor plus acetylene can be in the range 0.1 bar (absolute) to 20.0 bar (absolute), e.g., 0.1 bar (absolute) to 5.0 bar (absolute); and the temperature can be in the range 100° C. to 500° C., e.g., 200° C. to 400° C. to avoid coking and other non-selective side reactions. Hydrogen partial pressure can be controlled to provide sufficient hydrogen for preventing catalyst coking, but not so much hydrogen as would significantly inhibit hydrogen donor dehydrogenation. Parameters such as total pressure, temperature, residence time, hydrogen-donor/acetylene molar ratio, and molecular hydrogen partial pressure, can be controlled so that the hydrogen transfer reaction is a net generator or consumer of hydrogen or is a net generator or consumer of heat.

In an embodiment, the pyrolysis step and oxidation steps are operated under conditions to (i) produce a second mixture comprising ≥5.0 wt. % acetylene and ≥1.0 wt. % ethane based on the weight of the second mixture and (ii) provide temperature and pressure in at least a portion of the second reactor suitable for catalytic hydrogen transfer. In that embodiment, this region of the second reactor can be loaded with a suitable hydrogen-transfer catalyst, e.g., by coating the inside surface of the reactor's honeycomb with a catalytically effective amount of at least one catalytic metal, to conduct at least a portion of an ethane-acetylene hydrogen-transfer reaction inside of stage 206.

Example

With reference to FIG. 2, the following simulation is performed. A first mixture comprising 0.3328 moles of methane, and 0.6655 moles of molecular hydrogen, is conducted to pyrolysis stage 206 and is isothermally exposed to a temperature of approximately 1500° C. at a total pressure of approximately 2.5 bar. 100.0 wt. % of the first mixture was subjected to the pyrolysis, and the conversion of the first mixture's methane to $C_2$ unsaturates is about 70% on a mole basis. In weight percents, the first mixture comprises 20 wt. % molecular hydrogen, 80 wt. % methane.

A second mixture is derived from the first mixture by the pyrolysis. The second mixture comprises 0.8198 moles of molecular hydrogen, 0.0825 moles methane, 0.0770 moles acetylene, and 0.0193 moles of ethylene per mole of the second mixture, and a small amount of coke which remains in the pyrolysis reactor. Except for the coke, the second mixture is conducted away from stage 206 via conduit 2065. In stage 208, hydrogen may be removed from the second mixture to produce an upgraded second mixture comprising 0.3572 moles of molecular hydrogen, 0.2944 moles of methane, 0.2748 moles of acetylene, and 0.0687 moles of ethylene per mole of the upgraded second mixture; this is conducted away from stage 208 via conduit 2081. The third mixture, thus derived from the second mixture by separations and the addition of propane, comprises 0.0869 moles of methane, 0.0811 moles of acetylene, 0.0203 moles of ethylene and 0.8117 moles of propane per mole of the third mixture. In stage 210, the third mixture is exposed to a hydrogen transfer catalyst comprising chromia at a temperature of 550° C. and a pressure of 5.8 bar (absolute) to produce a hydrogen-transfer product comprising 0.0406 moles of acetylene, 0.0608 moles of ethylene, 0.0869 moles of methane, 0.7712 moles of propane, and 0.0406 moles of propylene per mole of the hydrogen-transfer product. The acetylene conversion of the third mixture is 50% on a mole basis. Following separations, propane and unreacted acetylene could be recycled back to the hydrogen transfer reactor for increased conversion to olefins.

What is claimed is:

1. A hydrocarbon conversion process, comprising:
    (a) providing a first mixture comprising ≥10.0 wt. % hydrocarbon based on the weight of the first mixture;
    (b) conducting a pyrolysis by exposing the first mixture in a first region to a temperature ≥1200° C. under pyrolysis conditions to produce a second mixture, the second mixture comprising ≥1.0 wt. % acetylene, based on the weight of the second mixture;
    (c) conducting a hydrogen transfer in the presence of a hydrogen transfer catalyst under process conditions from a hydrogen donor comprising propane to at least 10.0 wt. % of the second mixture's acetylene to produce (i) ethylene from at least a portion of acetylene and (ii) propylene from at least a portion of the propane, the weight percent being based on the weight of the second mixture's acetylene,
    wherein the hydrogen transfer is exothermic and at least a portion of the heat released during the hydrogen transfer is utilized for heating at least a portion of the first mixture upstream of the pyrolysis;
    (d) separating a third mixture comprising at least a portion of the second mixture's acetylene from the second mixture;
    (e) providing first and second reactants, the first reactant comprising fuel and the second reactant comprising oxidant; and
    (f) combining at least a portion of the first reactant comprising fuel and at least a portion of the second reactant comprising oxidant in a second region to produce a fourth mixture by conducting an oxidation, the second region being at least partially coextensive with the first region, and at least partially oxidizing the fourth mixture's fuel component in the second region to produce heat and a fifth mixture comprising water and/or carbon dioxide; wherein the pyrolysis and the oxidation occur at different times.

2. The process of claim 1, wherein (i) the hydrogen donor comprises ≥90.0 wt. % of $C_{2+}$ alkane based on the weight of the hydrogen donor and (ii) ≥50.0 wt. % of the second mixture's acetylene is converted to ethylene by the hydrogen transfer of step (c).

3. The process of claim 1, wherein the first mixture's hydrocarbon comprises ≥10.0 wt. % carbon atoms included in aromatic rings based on the weight of the first mixture's hydrocarbon.

4. The process of claim 1, wherein the hydrogen donor comprises ≥90.0 wt. % propane based on the weight of the hydrogen donor; the process further comprising utilizing the hydrogen transfer of step (c) to produce (i) ethylene from at least a portion of the acetylene and (ii) propylene from at least a portion of the propane.

5. The process of claim 1, further comprising polymerizing at least a portion of the ethylene and/or at least a portion of the propylene.

6. The process of claim 1, further comprising (i) providing a source material, the source material comprising ≥10.0 wt. % methane and ≥1.0 wt. % ethane based on the weight of the source material and (ii) deriving the first mixture from the source material by separating at least a portion of the source material's ethane, the first mixture's hydrocarbon comprising ≥10.0 wt. % methane based on the weight of the first mixture's hydrocarbon; wherein the hydrogen donor further comprises ≥10.0 wt. % separated ethane based on the weight of the hydrogen donor.

7. The process of claim 6, further comprising utilizing the hydrogen transfer of step (c) to produce ethylene from at least a portion of each of (i) the acetylene and (ii) the separated ethane.

8. The process of claim 7, further comprising polymerizing at least a portion of the ethylene.

9. The process of claim 1, wherein the second mixture has an acetylene:ethylene molar ratio ≥2.0.

10. The process of claim 1, further comprising utilizing at least a portion of the third mixture's acetylene for the hydrogen transfer.

11. The process of claim 1, wherein the pyrolysis is conducted under high severity conditions including a total pressure ≥0.1 bar (absolute), a residence time ≤0.05 seconds, and the temperature ≥$1.40 \times 10^{3}$° C.

12. The process of claim 1, further comprising repeating steps (a)-(f) in sequence, wherein (i) at least a portion of the fifth mixture is conducted away from the second region before step (a) and (ii) the at least a portion of the heat is utilized in the first region for the pyrolysis.

13. The process of claim 1, wherein the hydrogen transfer catalyst comprises (i) one or more metals selected from Group VIb of the Periodic Table, including oxides and sulfides thereof and/or (ii) one or more metals selected from Group VIII of the Periodic Table, including oxides and sulfides thereof.

14. The process of claim 1, wherein the hydrogen transfer is conducted under process conditions include a total pressure in the range of from 0.3 to 20.0 bar absolute, a partial pressure of hydrogen donor plus acetylene in the range of from 0.1 to 10.0 bar absolute, and a temperature in the range of from 200° C. to 500° C.

15. The process of claim 1, wherein the second mixture further comprises ≥1.0 wt. % of molecular hydrogen.

16. The process of claim 15, wherein the hydrogen transfer is conducted in the presence of at least a portion of the second mixture's molecular hydrogen.

17. The process of claim 1, wherein the first mixture's hydrocarbon comprises ≥50.0 wt. % of methane and/or carbon atoms included in aromatic rings based on the weight of the first mixture's hydrocarbon.

* * * * *